United States Patent
Kong et al.

(10) Patent No.: US 11,504,087 B2
(45) Date of Patent: Nov. 22, 2022

(54) ULTRASONIC DIAGNOSTIC DEVICE AND CONTROL METHOD THEREFOR

(71) Applicant: SAMSUNG MEDISON CO., LTD., Gangwon-Do (KR)

(72) Inventors: Dong-geon Kong, Hwaseong-si (KR); Seong-hyeon Choi, Seoul (KR); Hyoung-ki Lee, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 873 days.

(21) Appl. No.: 16/093,372

(22) PCT Filed: Nov. 4, 2016

(86) PCT No.: PCT/KR2016/012636
§ 371 (c)(1),
(2) Date: Oct. 12, 2018

(87) PCT Pub. No.: WO2017/179782
PCT Pub. Date: Oct. 19, 2017

(65) Prior Publication Data
US 2019/0125300 A1 May 2, 2019

(30) Foreign Application Priority Data
Apr. 12, 2016 (KR) ........................ 10-2016-0044936

(51) Int. Cl.
*A61B 8/00* (2006.01)
*A61B 8/08* (2006.01)
*A61B 5/00* (2006.01)

(52) U.S. Cl.
CPC ................. *A61B 8/42* (2013.01); *A61B 5/00* (2013.01); *A61B 8/08* (2013.01); *A61B 8/4411* (2013.01);
(Continued)

(58) Field of Classification Search
CPC .... A61B 8/42; A61B 5/00; A61B 8/56; A61B 8/58; A61B 8/488; A61B 8/4411;
(Continued)

(56) References Cited

U.S. PATENT DOCUMENTS 6,585,666 B2 7/2003 Suh et al.
7,914,456 B2 3/2011 Osaka et al.
(Continued)

FOREIGN PATENT DOCUMENTS

EP 2995259 A1 3/2016
JP H09-085445 A 3/1997
(Continued)

OTHER PUBLICATIONS

International Search Report dated Feb. 20, 2017 issued in International Patent Application No. PCT/KR2016/012636 (with English translation).
(Continued)

*Primary Examiner* — Christopher Koharski
*Assistant Examiner* — Taylor Deutsch
(74) *Attorney, Agent, or Firm* — Morgan, Lewis & Bockius LLP

(57) ABSTRACT

Provided is an ultrasound diagnostic apparatus including a probe configured to induce displacement in tissue of an object by irradiating a first focused beam of a first frequency to the object; and a processor configured to obtain a first ultrasound image of the object in which displacement has been induced; to determine whether the induced displacement is appropriate based on the obtained first ultrasound image; when the induced displacement is not appropriate, to control the probe to irradiate a second focused beam of a second frequency different from the first frequency to the object, so as to induce displacement in the tissue of the object; and to process a second ultrasound image of the
(Continued)

object in which displacement has been induced by the second focused beam.

11 Claims, 11 Drawing Sheets

(52) U.S. Cl.
CPC ............ *A61B 8/4488* (2013.01); *A61B 8/463* (2013.01); *A61B 8/485* (2013.01); *A61B 8/488* (2013.01); *A61B 8/54* (2013.01); *A61B 8/56* (2013.01); *A61B 8/58* (2013.01); *A61B 8/4427* (2013.01)

(58) Field of Classification Search
CPC ....... A61B 8/4488; A61B 8/463; A61B 8/485; A61B 8/54; A61B 8/08; A61B 8/4427; A61B 5/0053; A61B 8/0891; A61B 8/5223; A61B 8/5276
See application file for complete search history.

(56) References Cited

U.S. PATENT DOCUMENTS

| | | | |
|---|---|---|---|
| 8,007,438 B2 | 8/2011 | Osaka et al. | |
| 8,469,888 B2 | 6/2013 | Lee et al. | |
| 8,747,320 B2 | 6/2014 | Matsumura | |
| 10,779,799 B2 * | 9/2020 | Chen | G01S 7/52077 |
| 2005/0085728 A1 | 4/2005 | Fukuda | |
| 2010/0240994 A1 | 9/2010 | Zheng | |
| 2011/0028838 A1 | 2/2011 | Pernot et al. | |
| 2012/0157831 A1 | 6/2012 | Waki | |
| 2013/0317361 A1 * | 11/2013 | Tabaru | G01S 7/52042 600/438 |
| 2013/0345565 A1 * | 12/2013 | Fan | A61B 8/08 600/442 |
| 2014/0343419 A1 * | 11/2014 | Sako | A61B 8/5292 600/437 |
| 2015/0119710 A1 * | 4/2015 | Kawae | A61B 8/14 600/438 |
| 2015/0148674 A1 | 5/2015 | Park et al. | |
| 2015/0297175 A1 | 10/2015 | Kanayama et al. | |

FOREIGN PATENT DOCUMENTS

| | | |
|---|---|---|
| JP | 2010-082337 A | 4/2010 |
| JP | 2011-120614 A | 6/2011 |
| KR | 10-0317811 | 12/2001 |
| KR | 10-2010-0000881 A | 1/2010 |
| KR | 10-2012-0071385 A | 7/2012 |
| KR | 10-2015-0061989 A | 6/2015 |

OTHER PUBLICATIONS

Extended European Search Report dated Mar. 22, 2019 issued in European Patent Application No. 16898744.4.

* cited by examiner (S302)     (S304)

(S306)

ULTRASONIC DIAGNOSTIC DEVICE AND CONTROL METHOD THEREFOR

CROSS REFERENCE

This patent application is the U.S. National Phase under 35 U.S.C. § 371 of International Application No. PCT/KR2016/012636, filed on Nov. 4, 2016, which claims the benefit of Korean Patent Application No. 10-2016-0044936, filed on Apr. 12, 2016, the entire contents of each are hereby incorporated by reference.

TECHNICAL FIELD

Disclosed embodiments relate to an ultrasound diagnostic apparatus, an ultrasound diagnostic apparatus control method, and a computer-readable recording medium storing program codes for performing the ultrasound diagnostic apparatus control method.

BACKGROUND ART

Recently, in the medical field, various types of medical imaging apparatuses for imaging and obtaining information about biological tissue of the human body have been widely used for early diagnosis or surgical treatment of diseases. Representative examples of medical imaging apparatuses may include an ultrasound diagnostic apparatus, a computed tomography (CT) apparatus, and a magnetic resonance imaging (MRI) apparatus.

Ultrasound diagnostic apparatuses transmit ultrasound signals generated by transducers of a probe to an object and receive echo signals reflected from the object, thereby obtaining an image of an internal part of the object. In particular, ultrasound diagnostic apparatuses are used for medical purposes including observation of the interior of an object, detection of foreign substances, and diagnosis of damage to the object. Such ultrasound diagnostic apparatuses provide high stability, display images in real time, and are safe due to the lack of radioactive exposure, compared to diagnostic apparatuses using X-rays. Therefore, ultrasound diagnostic apparatuses are widely used together with other diagnostic imaging apparatuses.

In addition, an ultrasound diagnostic apparatus may support a brightness (B) mode, a Doppler mode, an elastic mode, and the like. In the B mode, a reflection coefficient of an ultrasound signal is visualized as a two-dimensional (2D) image. In the Doppler mode, a velocity of a moving object (in particular, blood flow) is shown as an image by using the Doppler effect. In the elastic mode, a difference between responses when compression is applied or is not applied to an object is visualized as an image.

DESCRIPTION OF EMBODIMENTS

Technical Problem

Disclosed embodiments provide an apparatus and method for applying appropriate compression to an object so as to obtain an image of an elastic mode.

Also, disclosed embodiments are provided for without additional costs, receiving feedback on compression applied to an object and for applying appropriate compression to the object.

Solution to Problem

According to an aspect of the present disclosure, an ultrasound diagnostic apparatus includes a probe configured to induce displacement in tissue of an object by irradiating a first focused beam of a first frequency to the object; and a processor configured to obtain a first ultrasound image of the object in which displacement has been induced; to determine whether the induced displacement is appropriate based on the obtained first ultrasound image; when the induced displacement is not appropriate, to control the probe to irradiate a second focused beam of a second frequency different from the first frequency to the object, so as to induce displacement in the tissue of the object; and to process a second ultrasound image of the object in which displacement has been induced by the second focused beam.

When the displacement induced by the first focused beam is not appropriate, the processor may be further configured to adjust at least one of a voltage and a number of cycles of the second focused beam.

The probe may be further configured to induce displacement in the tissue by irradiating a third focused beam of a third frequency different from the first frequency to the object after the first focused beam is irradiated, and the processor may be further configured to determine the second frequency based on the first ultrasound image and the third ultrasound image, and to control the probe to irradiate the second focused beam of the determined second frequency to the object.

When an obstacle interfering movement of a shear wave induced by the displacement is detected in the second ultrasound image, the processor may be further configured to control the probe to change a horizontal focusing position of the second focused beam.

The ultrasound diagnostic apparatus may further include a display configured to display information about a focusing position of the focused beam, and information about variation in the focusing position.

The processor may be further configured to determine whether the induced displacement is appropriate based on at least one of a magnitude of the induced displacement, a quality index of an elastic image, and strain of the object, or a combination thereof.

The ultrasound diagnostic apparatus may further include an actuator configured to induce displacement by applying a mechanical force to the object.

The ultrasound diagnostic apparatus may further include a display configured to display at least one of an intensity for inducing displacement, a magnitude of an induced displacement, and strain, or information about a combination thereof.

According to another aspect of the present disclosure, an ultrasound diagnostic apparatus control method includes inducing displacement in tissue of an object by irradiating a first focused beam of a first frequency to the object; obtaining a first ultrasound image of the object in which displacement has been induced; determining whether the induced displacement is appropriate based on the obtained first ultrasound image; when the induced displacement is not appropriate, irradiating a second focused beam of a second frequency different from the first frequency to the object, so as to induce displacement in the tissue of the object; and obtaining a second ultrasound image of the object in which displacement has been induced by the second focused beam.

According to another aspect of the present disclosure, an ultrasound diagnostic apparatus includes a probe configured to induce displacement in tissue of an object by irradiating a first focused beam to the object; and a processor configured to obtain a first ultrasound image of the object in which displacement has been induced, to determine whether the induced displacement is appropriate based on the obtained first ultrasound image, when the induced displacement is not appropriate, to control the probe to irradiate a second focused beam having a focusing position different from the first focused beam to the object, so as to induce displacement in the tissue of the object, and to process a second ultrasound image of the object in which displacement has been induced by the second focused beam.

According to another aspect of the present disclosure, an ultrasound diagnostic apparatus control method includes inducing displacement in tissue of an object by irradiating a first focused beam to the object; obtaining a first ultrasound image of the object in which displacement has been induced; determining whether the induced displacement is appropriate based on the obtained first ultrasound image; when the induced displacement is not appropriate, irradiating a second focused beam having a focusing position different from the first focused beam to the object, so as to induce displacement in the tissue of the object; and obtaining a second ultrasound image of the object in which displacement has been induced by the second focused beam.

According to another aspect of the present disclosure, a computer-readable recording medium stores computer program codes for performing an ultrasound diagnostic apparatus control method according to the embodiments.

Advantageous Effects of Disclosure

According to disclosed embodiments, it is possible to apply appropriate compression to an object when an image of an elastic mode is obtained.

Also, according to disclosed embodiments, it is possible to without additional costs, receive feedback on compression applied to an object and to apply appropriate compression to the object

BRIEF DESCRIPTION OF DRAWINGS

The present disclosure will now be described more fully through the detailed descriptions below with reference to the accompanying drawings, in which reference numerals denote structural elements.

BEST MODE

Figure 1:
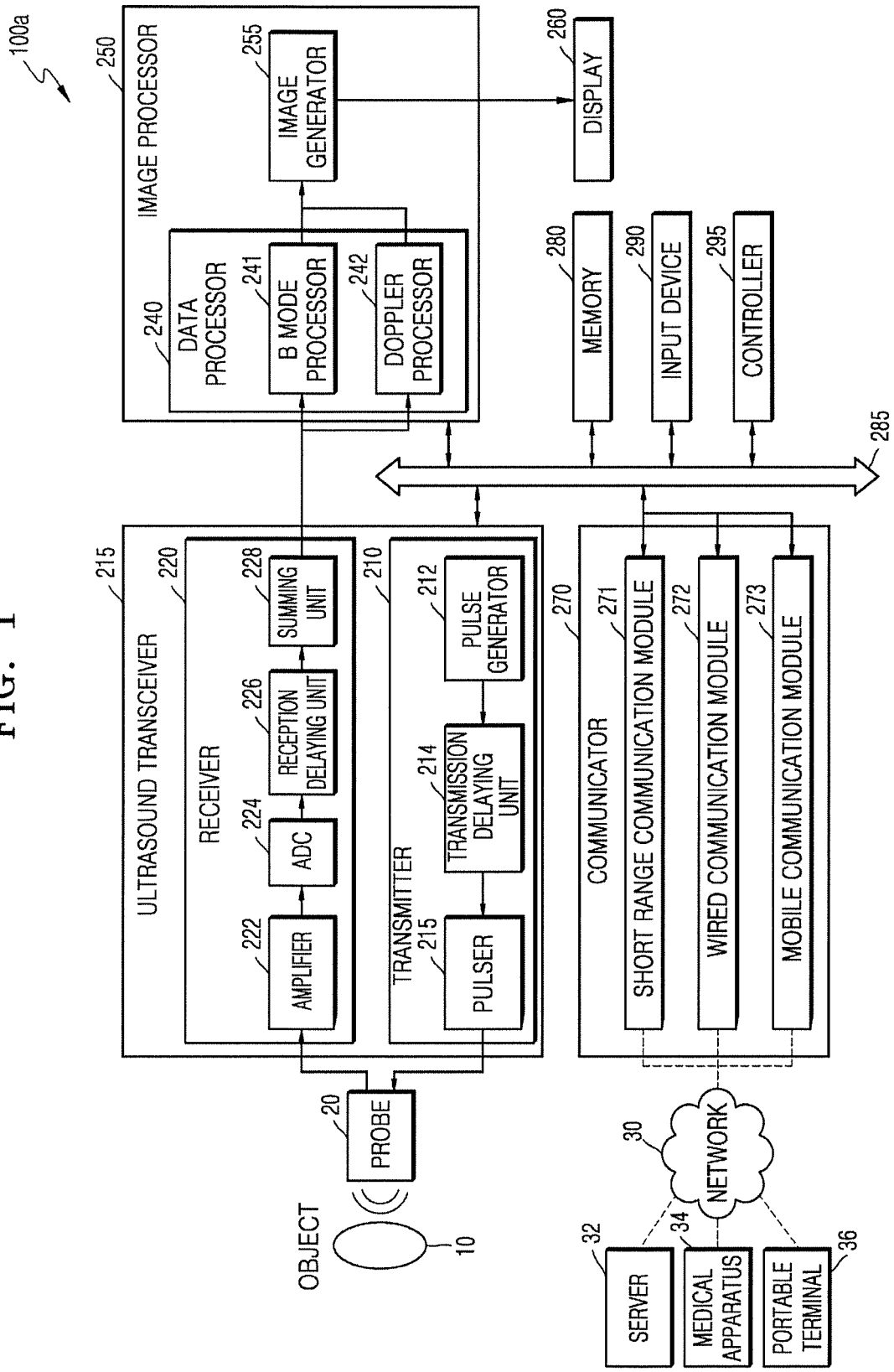
FIG. 1 is a block diagram illustrating a configuration of an ultrasound diagnostic apparatus 100a according to an embodiment.

According to an aspect of the present disclosure, an ultrasound diagnostic apparatus includes a probe configured to induce displacement in tissue of an object by irradiating a first focused beam of a first frequency to the object; and a processor configured to obtain a first ultrasound image of the object in which displacement has been induced; to determine whether the induced displacement is appropriate based on the obtained first ultrasound image; when the induced displacement is not appropriate, to control the probe to irradiate a second focused beam of a second frequency different from the first frequency to the object, so as to induce displacement in the tissue of the object; and to process a second ultrasound image of the object in which displacement has been induced by the second focused beam.

MODE OF DISCLOSURE

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the module may be embodied as hardware or software or embodied by combining hardware and software.

Throughout the specification, an "image" may refer to multi-dimensional data composed of discrete image elements. Examples of an image may include, but are not limited to, medical images, i.e., an ultrasound image, a computed tomography (CT) image, a magnetic resonance (MR) image respectively obtained by an ultrasound apparatus, a CT apparatus, and an MR imaging (MRI) apparatus.

Furthermore, an "object" may be a human, an animal, or a part of a human or animal. For example, the object may be an organ (e.g., the liver, the heart, the womb, the brain, a breast, or the abdomen), or a blood vessel. Also, the object may be a phantom. The phantom may refer to a material having a density, an effective atomic number, and a volume that are approximately the same as those of an organism. For example, the phantom may be a spherical phantom having properties similar to a human body.

An ultrasound image may be an image obtained by transmitting ultrasound signals generated by transducers of a probe to an object and receiving information about echo signals reflected from the object. Furthermore, an ultrasound image may be variously realized. For example, the ultrasound image may be at least one of an amplitude (A) mode image, a brightness (B) mode image, a color (C) mode image, and a Doppler (D) mode image. In addition, according to an embodiment of the present disclosure, an ultrasound image may be a two-dimensional (2D) or three-dimensional (3D) image. Also, an ultrasound image includes radio frequency (RF) data and in-phase quadrature (IQ) data. The RF data may include channel RF data output from an analog-to-digital converter, and beam-formed RF data obtained by performing beamforming processing on the channel RF data. The IQ data is obtained by performing mixing processing on beam-formed RF data by transforming a center frequency to 0 Hz.

Throughout the specification, a "user" may be, but is not limited to, a medical expert, for example, a medical doctor, a nurse, a medical laboratory technologist, or a medical imaging expert, or a technician who repairs medical apparatuses.

The present disclosure will now be described more fully with reference to the accompanying drawings for one of ordinary skill in the art to be able to perform the present disclosure without any difficulty. The present disclosure may, however, be embodied in many different forms and should not be construed as being limited to the embodiments set forth herein.

FIG. 1 is a block diagram illustrating a configuration of an ultrasound diagnostic apparatus 100a according to an embodiment.

Referring to FIG. 1, the ultrasound diagnostic apparatus 100a according to an embodiment may include a probe 20, an ultrasound transceiver 215, an image processor 250, a communicator 270, a display 260, a memory 280, an input device 290, and a controller 295, and the aforementioned elements may be connected to each other via a bus 285.

The ultrasound diagnostic apparatus 100a according to an embodiment may be implemented as a cart-type apparatus or a portable-type apparatus. Examples of a portable-type ultrasound diagnostic apparatus may include, but are not limited to, a picture archiving and communication system (PACS) viewer, a smartphone, a laptop computer, a personal digital assistant (PDA), a tablet PC, or the like.

The probe 20 transmits an ultrasound signal to an object 10 in response to a driving signal applied by the ultrasound transceiver 215, and receives an echo signal reflected from the object 10. The probe 20 includes a plurality of transducers, and the plurality of transducers oscillate in response to transferred electric signals and generate acoustic energy, that is, ultrasound waves. Also, the probe 20 may be connected to a main body of the ultrasound diagnostic apparatus 100a in a wired or wireless manner, and according to embodiments, the ultrasound diagnostic apparatus 100a may include a plurality of probes 20.

A transmitter 210 supplies a driving signal to the probe 20, and includes a pulse generator 212, a transmission delaying unit 214, and a pulser 216. The pulse generator 212 generates pulses for forming transmission ultrasound waves based on a certain pulse repetition frequency (PRF), and the transmission delaying unit 214 applies delay times to the pulses, the delay times being necessary for determining transmission directionality. The pulses to which the delay times have been applied respectively correspond to a plurality of piezoelectric vibrators included in the probe 20. The pulser 216 applies a driving signal (or a driving pulse) to the probe 20 based on timing corresponding to each of the pulses to which the delay times have been applied.

A receiver 220 generates ultrasound data by processing the echo signals received from the probe 20, and may include an amplifier 222, an analog-to-digital converter (ADC) 224, a reception delaying unit 226, and a summing unit 228. The amplifier 222 amplifies the echo signals in each channel, and the ADC 224 performs analog-to-digital conversion on the amplified echo signals. The reception delaying unit 226 applies delay times to digitized echo signals, the delay times being necessary for determining reception directionality, and the summing unit 228 generates ultrasound data by summing the echo signals processed by the reception delaying unit 226. In some embodiments, the receiver 220 may not include the amplifier 222. That is, when sensitivity of the probe 20 or the number of processable bits by the ADC 224 is increased, the amplifier 222 may be omitted. Also, the receiver 220 converts an ultrasound signal received from the probe 20 into a beamformed RF signal or an IQ signal by using a beamformer or the like.

The image processor 250 generates an ultrasound image by scan-converting ultrasound data generated by the ultrasound transceiver 215, and displays the ultrasound image.

The ultrasound image may be not only a grayscale ultrasound image obtained by scanning an object in an amplitude (A) mode, a brightness (B) mode, and a motion (M) mode, but may also be a Doppler image showing a movement of the object by using a Doppler effect. The Doppler image may include a blood flow Doppler image showing flow of blood (also referred to as a color flow image), a tissue Doppler image showing a movement of tissue, and a spectral Doppler image showing a moving speed of an object as a waveform.

A B mode processor 241 extracts B mode components from ultrasound data and processes the B mode components. An image generator 255 may generate an ultrasound image indicating signal intensities as brightness based on the B mode components extracted by the B mode processor 241.

Equally, a Doppler processor 242 may extract Doppler components from ultrasound data, and the image generator 255 may generate a Doppler image (e.g., a color flow image) indicating a movement of an object as colors or waveforms based on the extracted Doppler components.

The image generator 255 may generate a 3D ultrasound image via a volume rendering process with respect to volume data and may also generate an elastic image by imaging deformation of the object 10 due to compression. Furthermore, the image generator 255 may display various pieces of additional information on an ultrasound image by using text and graphics. In addition, the generated ultrasound image may be stored in the memory 280.

The display 260 may include at least one of a liquid crystal display (LCD), a thin film transistor-LCD (TFT-LCD), an organic light-emitting diode (OLED) display, a flexible display, a 3D display, and an electrophoretic display.

Furthermore, when the display 260 and a user interface form a layer structure to form a touchscreen, the display 260 may be used not only as an output device but may also be used as an input device via which a user inputs information via a touch.

The touchscreen may be configured to detect a position of a touch input, a touched area, and pressure of a touch. Also, the touchscreen may be configured to detect not only a real touch but also a proximity touch.

The communicator 270 is connected to a network 30 in a wired or wireless manner to communicate with an external device or a server. The communicator 270 may exchange data with a hospital server or another medical apparatus in a hospital, which is connected thereto via a PACS. Furthermore, the communicator 170 may perform data communication according to the digital imaging and communications in medicine (DICOM) standard.

The communicator 270 may transmit and receive data related to diagnosis of an object, e.g., an ultrasound image, ultrasound data, and Doppler data of the object, via the network 30 and may also transmit and receive medical images captured by another medical apparatus, e.g., a computed tomography (CT) apparatus, a magnetic resonance imaging (MRI) apparatus, or an X-ray apparatus. Furthermore, the communicator 270 may receive information about a diagnosis history or medical treatment schedule of a patient from a server and may use the received information to diagnose an object. Furthermore, the communicator 270 may perform data communication with not only a server or a medical apparatus in a hospital, but also with a portable terminal of a medical doctor or the patient.

The communicator 270 may be connected to the network 30 in a wired or wireless manner to exchange data with a server 32, a medical apparatus 34, or a portable terminal 36. The communicator 270 may include one or more components for communication with external devices. For example, the communicator 270 may include a short range communication module 271, a wired communication module 272, and a mobile communication module 273.

The short range communication module 271 refers to a module for short range communication within a certain distance. Examples of short range communication techniques according to an embodiment of the present disclosure may include, but are not limited to, wireless local area network (LAN), Wi-Fi, Bluetooth, Zigbee, Wi-Fi Direct (WFD), ultra-wideband (UWB), Infrared Data Association (IrDA), Bluetooth Low Energy (BLE), near field communication (NFC), or the like.

The wired communication module 272 refers to a module for communication using electric signals or optical signals. Examples of wired communication techniques according to an embodiment may include communication via a pair cable, a coaxial cable, an optical fiber cable, an Ethernet cable, or the like.

The mobile communication module 273 transmits and receives wireless signals to and from at least one of a base station, an external terminal, and a server on a mobile communication network. In this regard, the wireless signals may be voice call signals, video call signals, or various types of data for transmission and reception of text/multimedia messages.

The memory 280 stores various information processed by the ultrasound diagnostic apparatus 100a. For example, the memory 180 may store medical data related to diagnosis of an object, such as ultrasound data and an ultrasound image that are input or output, and may also store algorithms or programs which are to be executed in the ultrasound diagnostic apparatus 100a.

The memory 280 may be implemented as one of various storage media including a flash memory, a hard disk drive, an electrically erasable programmable read-only memory (EEPROM), or the like. Furthermore, the ultrasound diagnostic apparatus 100a may run web storage or a cloud server that performs the storage function of the memory 280 on the Internet.

The input device 290 refers to a means via which a user inputs data for controlling the ultrasound diagnostic apparatus 100a. The input device 290 may include, but is not limited to, hardware components such as a keypad, a mouse, a touch pad, a track ball, a jog switch, or the like. Furthermore, the input device 290 may include a fingerprint recognition sensor to detect a user's fingerprint. In addition, the input device 290 may further include various other components including an electrocardiogram (ECG) measuring module, a respiration measuring module, a voice recognition sensor, a gesture recognition sensor, an iris recognition sensor, a depth sensor, a distance sensor, or the like. In particular, the input device 290 may also include a touchscreen in which a touch pad forms a layer structure with the display 260.

The ultrasound diagnostic apparatus 100a according to an embodiment may display an ultrasound image in a certain mode and a control panel for the ultrasound image on the touchscreen. The ultrasound diagnostic apparatus 100a may also detect a user's touch gesture with respect to the ultrasound image via the touchscreen.

According to an embodiment, the ultrasound diagnostic apparatus 100a may include some physical buttons that are frequently used by a user among buttons that are included in a control panel of a general ultrasound apparatus, and may provide other buttons in the form of a graphical user interface (GUI) via the touchscreen.

The controller 295 may control all operations of the ultrasound diagnostic apparatus 100a. The controller 295 may control operations among the probe 20, the ultrasound transceiver 215, the image processor 250, the communicator 270, the memory 280, and the input device 290.

The probe 20, the ultrasound transceiver 215, the image processor 250, the display 240, the communicator 270, the memory 280, the input device 290, and the controller 295 may be implemented as various combinations of one or more software modules and one or more hardware components. For example, the image processor 250 may include a plurality of software modules and a processor, the plurality of software modules operating due to program codes stored in the memory 280 and the processor processing the program codes. Also, at least some of the ultrasound transceiver 215, the image processor 250, and the communicator 270 may be included in the controller 295, but the present disclosure is not limited thereto.

Figure 2:
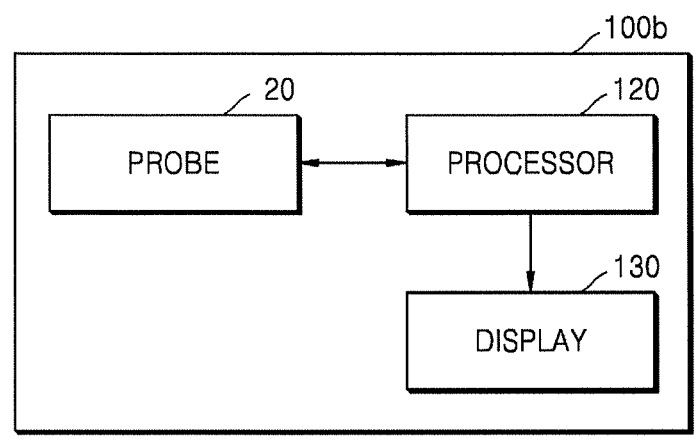
FIG. 2 is a block diagram illustrating a configuration of an ultrasound diagnostic apparatus 100b according to an embodiment.

FIG. 2 is a block diagram illustrating a configuration of an ultrasound diagnostic apparatus 100b according to an embodiment.

The ultrasound diagnostic apparatus 100b according to an embodiment includes the probe 20, a processor 120, and a display 130. According to some embodiments, the ultrasound diagnostic apparatus 100b may include the probe 20 and the processor 120 and may not include the display 130.

The processor 120 of FIG. 2 may correspond to at least one or a combination of the image processor 250 and the controller 295 of FIG. 1. The display 130 may correspond to the display 260 of FIG. 1. According to some embodiments, some of elements of the ultrasound diagnostic apparatus 100a shown in FIG. 1 may be included in the ultrasound diagnostic apparatus 100b shown in FIG. 2.

The probe 20 irradiates ultrasound waves to an object and detects an echo signal. Also, the probe 20 induces displacement with respect to the object. According to an embodiment, the probe 20 may induce displacement in the object by irradiating a focused beam to the object. The probe 20 may generate and output an ultrasound focused beam by controlling an ultrasound signal output sequence from piezoelectric devices arranged in an array structure. When the focused beam is irradiated to the object, deformation of the object occurs due to the focused beam such that displacement in tissue is induced. When the displacement in the object is induced, the ultrasound diagnostic apparatus 100a may image an ultrasound image and may obtain an ultrasound image of an elastic mode.

The processor 120 controls all operations of the ultrasound diagnostic apparatus 100b and processes data and signals. The processor 120 may be configured of one or more hardware units. According to an embodiment, the processor 120 may include individual hardware units configured to function as an image processor and a controller. The processor 120 may operate due to one or more software modules generated by executing program codes stored in the memory 280.

The processor 120 calculates displacement in movement of tissue from the obtained ultrasound image. For example, the displacement is calculated by comparing a plurality of ultrasound images obtained before and after compression is applied. The displacement may be calculated by performing auto-correlation or cross-correlation on ultrasound images obtained before and after movement of an object. As another example, the displacement may be calculated by using a difference image with respect to an ultrasound image or by differentiating the obtained ultrasound image with respect to time. Also, the processor 120 calculates strain by differentiating the calculated displacement in a depth direction. According to an embodiment, the processor 120 may include a module such as a displacement calculator, a strain calculator, or the like.

The processor 120 obtains a first ultrasound image of the object in which displacement has been induced, and determines whether the induced displacement is appropriate, based on the obtained ultrasound image. In a case where the probe 20 induces displacement by using a first setting value and the induced displacement is not appropriate, the processor 120 may control the probe 20 to induce displacement by using a second setting value different from the first setting value. The probe 20 repeats a process of including displacement by using the second setting value determined by the processor 120. After the probe 20 induces the displacement by using the second setting value, when the induced displacement is not appropriate, the processor 120 may set a third setting value different from the first setting value and the second setting value, and the probe 20 may induce displacement in an object 310 by using the third setting value.

A process of inducing displacement while changing a setting value may be repeatedly performed a plurality of times according to some embodiments, and a maximum number of repeating induction of displacement may be limited to some embodiments. For example, a maximum number of an operation of repeating induction of displacement may be preset in the ultrasound diagnostic apparatus 100b, the operation of repeating induction of displacement may be performed until a stop command is input by a user, or the maximum number may be set by a user.

The first setting value and the second setting value may be values about one or more parameters for controlling an operation, performed by the probe 20, of inducing displacement. Combinations of different values with respect to the one or more parameters may be defined as the first setting value and the second setting value. In a case where the operation, performed by the probe 20, of inducing displacement is controlled by combinations of a first parameter, a second parameter, and a third parameter, the processor 120 may define the second setting value by changing at least one value among values of the first parameter, the second parameter, and the third parameter which are defined for the first setting value.

According to some embodiments, whether an induced displacement is appropriate may be determined based on at least one of a magnitude of the induced displacement, strain, and a quality index, or a combination thereof. According to an embodiment, when a magnitude of displacement is less than a reference value, the processor 120 determines the displacement is not appropriate, and when a magnitude of displacement is equal to or greater than the reference value, the processor 120 determines the displacement is appropriate. According to another embodiment, the processor 120 may compare strain or a quality index with the reference value and then may determine whether a displacement is appropriate.

According to an embodiment, the ultrasound diagnostic apparatus 100b may operate in an elastic mode, and the ultrasound image may be an ultrasound image of the elastic mode.

The display 130 displays an operating state of the ultrasound diagnostic apparatus 100b, an ultrasound image, a user interface screen image, or the like. According to some embodiments, the display 130 may have one or more display panels. According to an embodiment, the display 130 may be embodied in the form of a touchscreen.

Hereinafter, an ultrasound diagnostic apparatus including embodiments disclosed in the present specification will now be referenced using reference numeral 100. However, even when reference numerals such as 100a and 100b are used for the ultrasound diagnostic apparatus according to embodiments of particular drawings, other embodiments are not excluded and it will be understood by one of ordinary skill in the art that features according to an embodiment may be applied to other embodiments to which the features are applicable.

Figure 3:
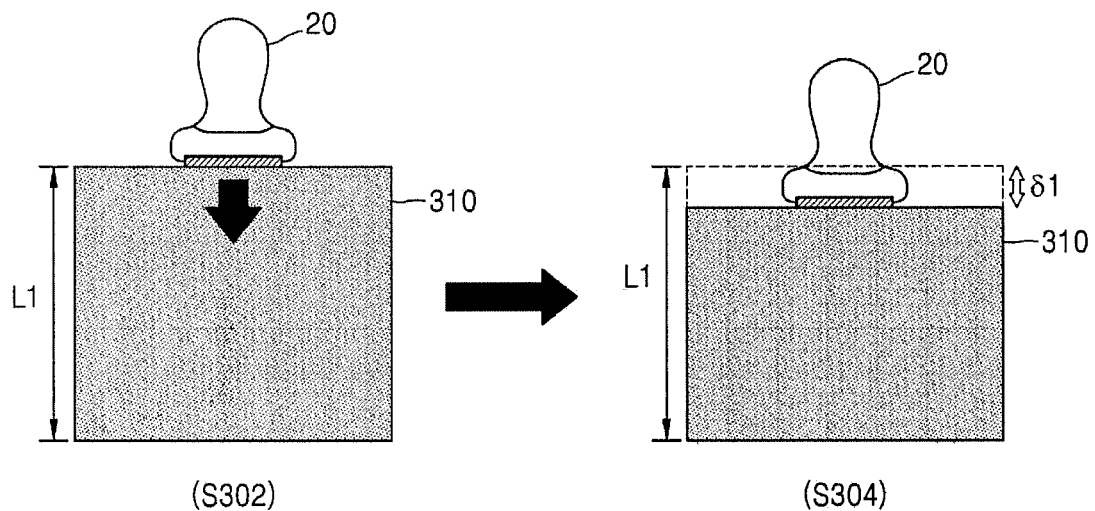
FIG. 3 is a diagram for describing a process of inducing displacement in an object 310.
Figure 3:
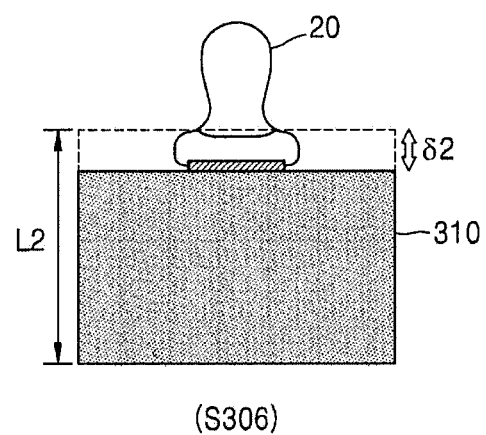

FIG. 3 is a diagram for describing a process of inducing displacement in the object 310.

To obtain an elastic image, displacement in the object 310 is induced by applying compression to the object 310. For example, as illustrated in S302 of FIG. 3, compression may be applied to the object 310 by pressing the object 310 by using the probe 20, and displacement 61 may be induced (S304). When the displacement 61 of the object 310 is induced, a length of the object 310 may be decreased in a compression direction. For example, as illustrated in S304 of FIG. 3, the length of the object 310 may be decreased from L1 to (L1−δ1) by being decreased by δ1. When the compression is applied to the object 310 and thus the displacement occurs, the displacement varies according to conditions of tissue in the object 310, and therefore a condition of the tissue may be diagnosed. Thus, a medical expert may examine the condition of the tissue by using an elastic image imaged when the displacement in the object 310 is induced.

The medical expert may measure an elastic feature of the tissue by using the elastic image. The elastic feature may be expressed as strain. The strain may be defined a ratio of displacement to an entire length of certain tissue of an object before the displacement occurs. For example, when the object 310 is deformed from a state of S302 to a state of S304 of FIG. 3, the strain may be defined as (δ1/L1). The strain may vary depending on objects. For example, at S306, a ratio of displacement δ2 to an entire length L2 of the certain tissue is greater than a case of S304, thus, a case of S306 has large strain.

As described above, to obtain an elastic image by inducing displacement in an object, the displacement in the object has to be induced by applying appropriate compression thereto. In a simple manner, a user of the ultrasound diagnostic apparatus 100 may apply compression to the object 310 by using the probe 20. However, when the user of the ultrasound diagnostic apparatus 100 applies compression to the object 310 by pressing the object 310 by using the probe 20, deviation occurs depending on users, thus, the elastic image may not be obtained. When compression applied to the object 310 is insufficient, a magnitude of induced displacement is small, thus, it is difficult to examine elasticity of the object, and when compression applied to the object 310 is excessive, a relation with respect to elasticity over compression enters a non-linear period, thus, it is difficult to clearly recognize an elastic feature of the object.

According to the embodiments, a setting value used in induction of displacement is adjusted based on an ultrasound image obtained after the ultrasound diagnostic apparatus 100 induces the displacement, and by doing so, deviation among users may be removed, and an inexperienced user may obtain a high quality elastic image.

Figure 4:
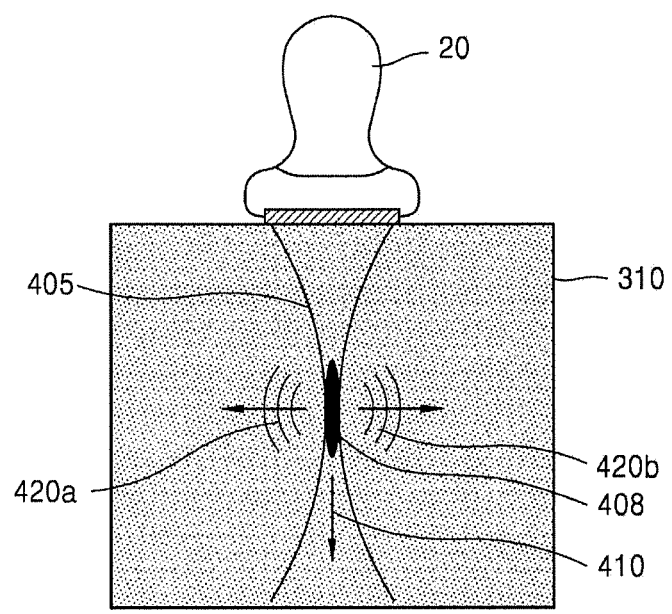
FIG. 4 is a diagram for describing a process of inducing displacement in an object, according to an embodiment.

FIG. 4 is a diagram for describing a process of inducing displacement in an object, according to an embodiment.

According to an embodiment, the probe 20 may induce displacement in the object 310 by irradiating an ultrasound focused beam 405 to the object 310. When the ultrasound focused beam 405 is irradiated to the object 310, displacement 410 in the object 310 is induced at a focusing position 408 at which the ultrasound focused beam 405 is focused. Due to the displacement 410 in the object 310, shear waves 420a and 420b are generated, the shear waves 420a and 420b moving from a generation point of the displacement 410 in a vertical direction of the displacement 410.

A mode of imaging shear waves of the object 310 is referred to as a shear wave elastic mode, and an ultrasound image captured in the shear wave elastic mode is referred to as a shear wave elastic image. To obtain a high-quality shear wave elastic image, it is required to induce the displacement 410 with an appropriate magnitude and the shear waves 420a and 420b from the object 310. Features of the induced displacement 410 and shear waves 420a and 420b vary according to the focusing position 408 of the focused beam 405, an amplitude or intensity of the focused beam 405, a frequency of the focused beam 405, the number of cycles, a transducer voltage, or the like. According to an embodiment, the processor 120 determines whether in induced displacement in the object 310 is appropriate, by using the obtained shear wave elastic image. When displacement induced based on a first setting value is not appropriate, the processor 120 defines a second setting value by changing at least one of a focusing position, a frequency, the number of cycles, and a transducer voltage, and the probe 20 induces displacement in tissue of an object by using the second setting value.

According to an embodiment, the first setting value and the second setting value are defined by frequencies. That is, the first setting value may be a first frequency, and the second setting value may be a second frequency different from the first frequency. The probe 20 irradiates an ultrasound focused beam of the first frequency to the object, and obtains a first ultrasound image of the object in which displacement has been induced. The processor 120 determines whether the induced displacement is appropriate, based on the first ultrasound image. When the induced displacement is not appropriate, the processor 120 control the probe 20 to irradiate an ultrasound focused beam of the second frequency to the object and to obtain a second ultrasound image of the object in which displacement has been induced.

The ultrasound diagnostic apparatus 100b according to an embodiment may determine a final setting value based on a plurality of ultrasound images obtained by inducing displacements by using focused beams of different setting values, may induce displacement by irradiating a focused beam of the final setting value to an object, and then may obtain an ultrasound image. According to an embodiment, the probe 20 induces displacement in an object by generating a first focused beam of a first setting value and irradiating the first focused beam to the object, and obtains a first ultrasound image of the object in which displacement has been induced. Next, the probe 20 induces displacement in the object by generating a third focused beam of a third setting value and irradiating the third focused beam to the object, and obtains a third ultrasound image of the object in which displacement has been induced. The processor 120 determines a second setting value based on the first ultrasound image and the third ultrasound image, generates a second focused beam of the second setting value, induces displacement in the object by irradiating the second focused beam to the object, and obtains a second ultrasound image of the object in which displacement has been induced.

According to an embodiment, the first setting value and the second setting value are defined by a combination of frequencies and voltage. The probe 20 irradiates an ultrasound focused beam of a first frequency and a first voltage to an object, and obtains a first ultrasound image of the object in which displacement has been induced. The processor 120 determines whether the induced displacement is appropriate, based on the first ultrasound image. When the induced displacement is not appropriate, the processor 120 controls the probe 20 to irradiate an ultrasound focused beam of a second frequency and to obtain a second ultrasound image of the object in which displacement has been induced.

In a case where an obstacle such as a cyst, blood vessels, or the like is present at the focusing position 408 of the focused beam 405, a shear wave is not induced such that a quality of a shear wave elastic image deteriorates. This is because the shear wave is not well induced in liquid. In this case, the processor 120 may set the second setting value to change the focusing position 408 of the focused beam 405, and the probe 20 may induce displacement in the tissue of the object by using the second setting value. According to an embodiment, the processor 120 may determine whether the induced displacement is appropriate, by using a quality index of shear wave elasticity. The quality index may also be referred to as a reliability index (RI), a reliability measurement index (RMI), or a cost function. The processor 120 obtains an ultrasound image by inducing a shear wave in the object, and calculates a shear wave speed by using the ultrasound image. Also, the processor 120 calculates a residual value by comparing an observed shear wave with a wave equation. When the shear wave speed is small, the processor 120 determines a first reliability score to be low, and when the residual value is large, the processor 120 determines a second reliability score to be low. The processor 120 calculates the quality index by using the first reliability score and the second reliability score.

A first reliability score $score_u$ to be determined by the shear wave speed may be defined by using Equation 1.

$$score_u = \left(\frac{0.2}{u_{max} - u_{min}}\right) \times u - \left(\frac{0.2 \times u_{min}}{u_{max} - u_{min}}\right) \quad \text{[Equation 1]}$$

In this regard, $u_{max}$ and $u_{min}$ are preset values, and u refers to observed displacement.

A shear wave satisfies the wave equation of Equation 2, but when an error included in an observed shear wave is increased, a residual value res of Equation 3 is increased.

$$\frac{\partial^2 u}{\partial t^2} - c^2 \nabla^2 u = 0 \quad \text{[Equation 2]}$$

$$res = \sum \left| \frac{\partial^2 u}{\partial t^2} - c^2 \nabla^2 u \right|^2 \quad \text{[Equation 3]}$$

In this regard, t refers to time, c refers to an ultrasound speed, and $\nabla 2$ is Laplacian.

A residual value may be standardized using Equation 4, and a standardized residual value $res_n$ may be calculated, such that a value corresponding to a signal-to-noise ratio (SNR) may be achieved.

$$res_n = \frac{\sum \left| \frac{\partial^2 u}{\partial t^2} - c^2 \nabla^2 u \right|^2}{\sum |\nabla^2 u|^2} \quad \text{[Equation 4]}$$

A second reliability score $score_{res}$ may be calculated by using Equation 5 using the standardized residual value.

$$score_{res} = -\left( \frac{0.8}{res_{max} - res_{min}} \right) \times res_n + \left( \frac{0.8 \times res_{max}}{res_{max} - res_{min}} \right) \quad \text{[Equation 5]}$$

In this regard, $res_{max}$ and $res_{min}$ are predefined parameters.

A final reliability score RI may be defined by using Equation 6. According to some embodiments, the final reliability score RI may be calculated by applying a weight to the first reliability score $score_u$ and the second reliability score $score_{res}$ and summing the weighted first reliability score $score_u$ and the weighted second reliability score $score_{res}$.

$RI = score_u + score_{res}$ $0 < score_u < 0.2$ $0 < score_{res} < 0.8$ [Equation 6]

The processor 120 may compare the final reliability score RI with a reference value and then may determine whether induced displacement is appropriate. For example, when the final reliability score RI is less than the reference value, the processor 120 may determine that the induced displacement is not appropriate.

Figure 5:
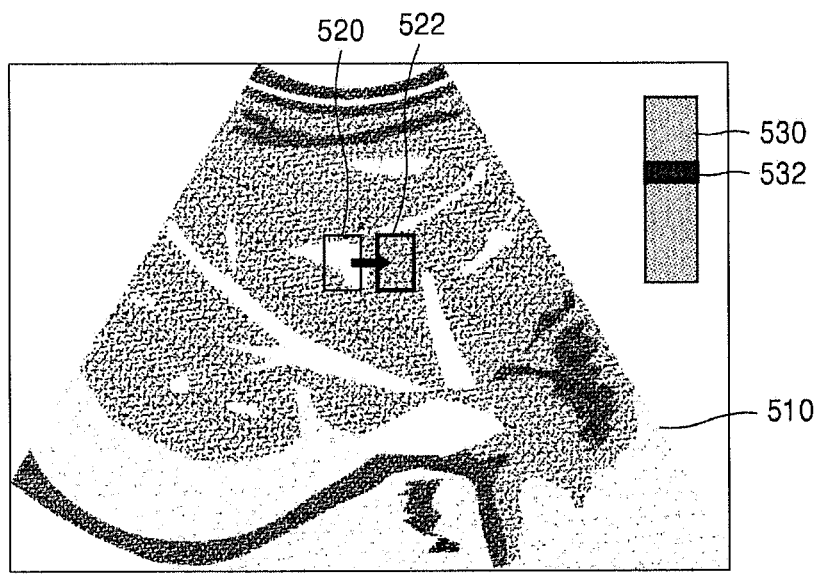
FIG. 5 illustrates a view displayed on a display 130, according to an embodiment.

FIG. 5 illustrates a view displayed on the display 130, according to an embodiment.

According to an embodiment, the display 130 may display an obtained ultrasound image 510 and information about a displacement inducing operation. According to an embodiment, the display 130 displays a first focusing position 520 of a focused beam on the ultrasound image 510. When displacement induced by a first focused beam at the first focusing position 520 is not appropriate, the processor 120 changes a focusing position of the focused beam to a second focusing position 522 by changing the focusing position, and the probe 20 induces displacement in an object by positioning a focus of a second focused beam at the second focusing position 522. In this case, the display 130 displays information about the second focusing position 522 on the ultrasound image 510. According to an embodiment, both information about the first focusing position 520 and information about the second focusing position 522 may be displayed to provide a user with information about variation in focusing positions.

According to an embodiment, the processor 120 adjusts a vertical focusing position of the focused beam 405, and when the focused beam 405 reaches a desired vertical focusing position, the processor 120 may adjust a horizontal focusing position. Even when the focused beam 405 is equally irradiated, a focusing position varies according to objects. This is because a condition of tissue, a feature, or the like are different in the objects. The processor 120 adjusts a frequency and then adjusts the vertical focusing position to correspond to a target vertical position at which displacement is to be induced. In this regard, the vertical focusing position refers to a depth from the probe 20 in a direction toward the object. When the vertical focusing position is adjusted to correspond to the target vertical position, the processor 120 adjusts the horizontal focusing position, based on an obtained shear wave elastic image. The horizontal focusing position refers to adjusting the focusing position while a height of the focusing position of the focused beam is maintained as illustrated in FIG. 5.

According to an embodiment, the display 130 may display at least one of a magnitude of displacement, a quality index of shear wave elasticity, and intensity of a focused beam, or a combination thereof. For example, as illustrated in FIG. 5, a graphical user interface view may include an indicator 532 in a box 530 indicating an entire range of quality indexes of shear wave elasticity, the box 530 indicating a value of a quality index of shear wave elasticity which is calculated from an ultrasound image.

The processor 120 may adjust the focusing position by adjusting an ultrasound signal output sequence of a transducer array of the probe 20.

Figure 6:
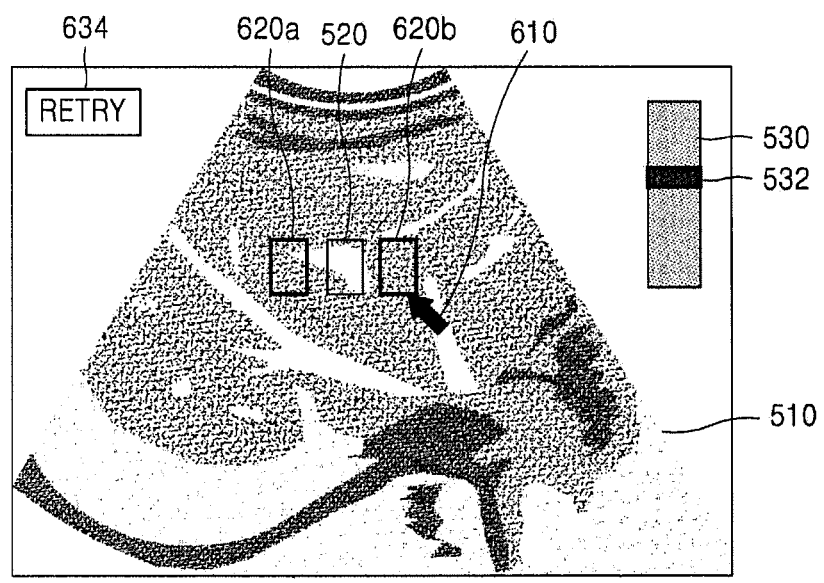
FIG. 6 illustrates a view displayed on the display 130, according to an embodiment.

FIG. 6 illustrates a view displayed on the display 130, according to an embodiment.

According to an embodiment, when induced displacement in an object is not appropriate, the processor 120 may provide a graphical user interface for selecting a focusing position of a focused beam to be used in re-inducing displacement. When the induced displacement in the object is not appropriate, the display 130 may display an indicator 634 indicating that the induced displacement is not appropriate.

According to an embodiment, as illustrated in FIG. 6, an indicator indicating the focusing position 520 according to a first setting value is displayed on the ultrasound image 510, and as candidates of a focusing position according to a second setting value, indicators indicating a first candidate position 620a and a second candidate position 620b are displayed on the display 130. A user may set the second setting value by selecting one of the first candidate position 620a and the second candidate position 620b by using a cursor 610.

Figure 7:
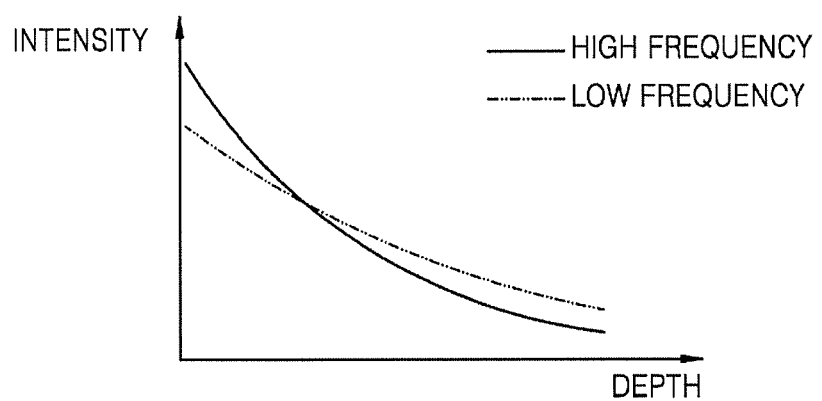
FIG. 7 is a diagram for describing a process of adjusting a frequency of a focused beam, according to an embodiment.

FIG. 7 is a diagram for describing a process of adjusting a frequency of a focused beam, according to an embodiment. FIG. 7 illustrates a relation between a distance DEPTH from a focused beam source and intensity INTENSITY of a focused beam with respect to a high frequency focused beam and a low frequency focused beam. In a graph of FIG. 7, a horizontal axis is defined as the distance DEPTH from the focused beam source, and a vertical axis is defined as the intensity INTENSITY of the focused beam.

According to an embodiment, when the probe 20 induces displacement in an object by using a focused beam, intensity of the focused beam may be adjusted by a frequency. An acoustic radiation force that involves causing displacement is proportional to the intensity. Equation 7 refers to an acoustic radiation force (F).

$$F = \frac{2\alpha I}{c} \quad \text{[Equation 7]}$$

In this regard, F refers to an acoustic radiation force, I refers to intensity of a focused beam, c refers to a speed of ultrasound waves, and α refers to an attenuation coefficient.

Intensity I(x) of the focused beam at a position x is defined by using Equation 8.

$$I(x)=I_0 \times e^{-\alpha f x} \quad \text{[Equation 8]}$$

In this regard, $I_0$ refers to intensity of a focused beam output from the probe 20, e refers to a natural constant, α refers to an attenuation coefficient, f refers to a frequency, and x refers to a depth.

When the depth is small and the focused beam has a center frequency, the intensity is at its peak. When the depth is large and attenuation is large, the intensity is large at a low frequency. In a case of a patient with high attenuation, it is preferable to further decrease a frequency than a normal case so as to induce large displacement. Thus, when displacement is less than a reference value, the processor 120 may increase intensity of a focused beam at a certain position by decreasing a frequency, and may increase displacement.

According to an embodiment, the processor 120 may adjust intensity of a focused beam by adjusting a voltage to be applied to transducers. Also, the processor 120 may adjust the intensity of the focused beam by adjusting the number of cycles of the focused beam.

Figure 8:
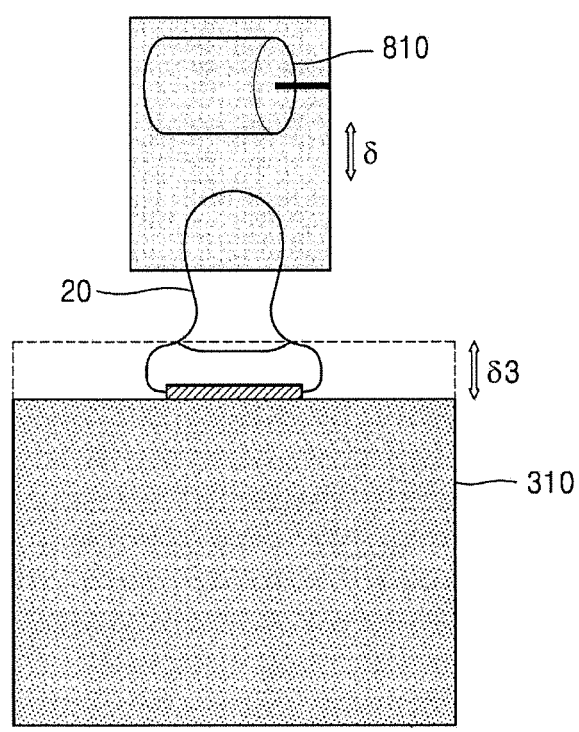
FIG. 8 is a diagram illustrating induction of displacement in an object, according to an embodiment.

FIG. 8 is a diagram where displacement in an object is induced, according to an embodiment.

According to an embodiment, the ultrasound diagnostic apparatus 100b includes an actuator 810 to induce displacement by applying a mechanical force to an object. The actuator 810 may be embodied in the form of a motor, a water balloon, an air bag, or the like, which converts electric energy into a mechanical force. The actuator 810 may be positioned adjacent to the probe 20 and may apply the mechanical force to the probe 20. The probe 20 is moved by the actuator 810 and applies compression to the object 310, and displacement 63 of the object 310 is induced due to the compression from the probe 20.

Figure 9:
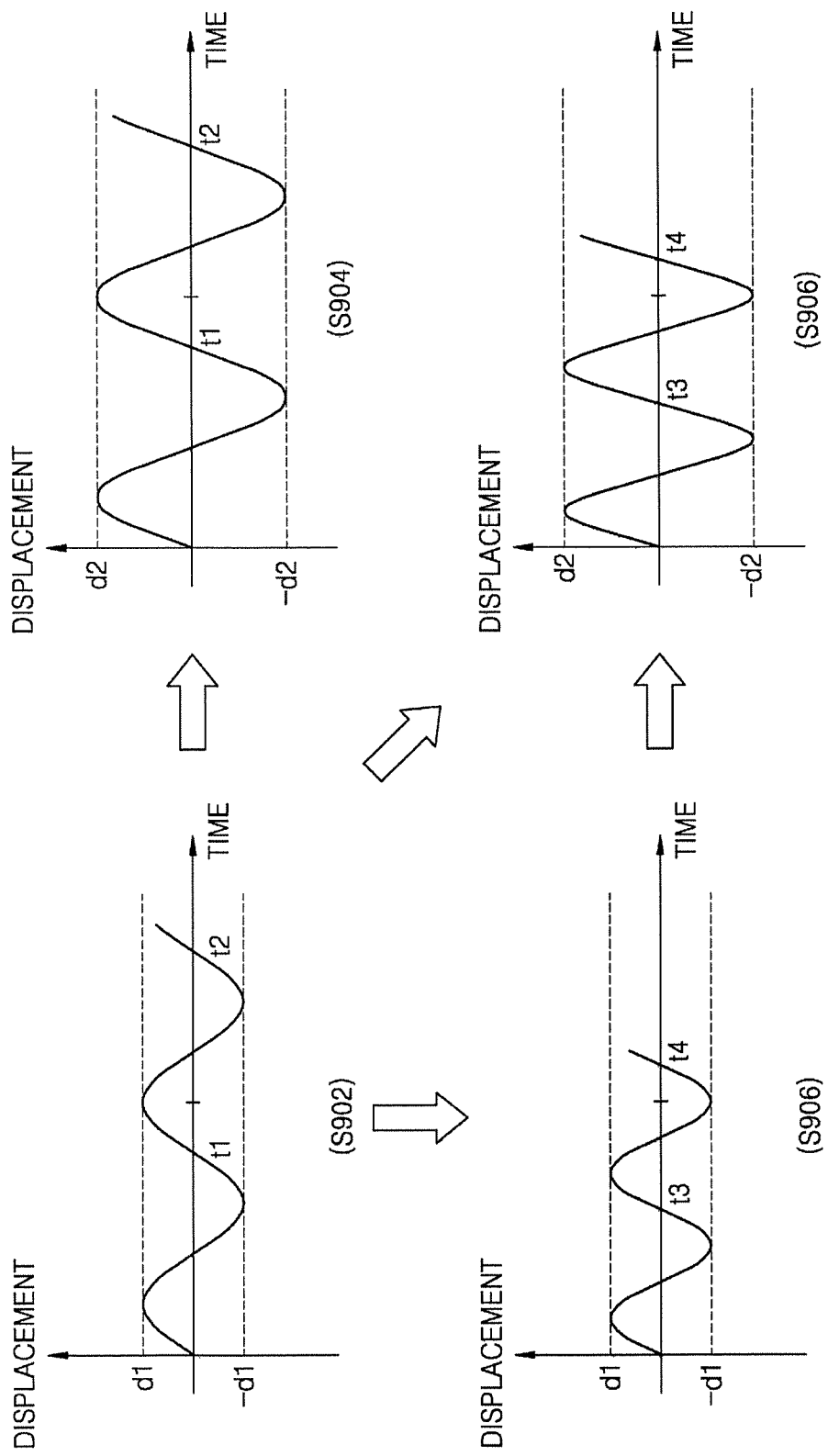
FIG. 9 is a diagram for describing a process of adjusting displacement induced by an actuator 810, according to an embodiment.

FIG. 9 is a diagram for describing a process of adjusting displacement induced by the actuator 810, according to an embodiment. FIG. 9 illustrates four graphs of displacement according to time of the actuator 810. In the graphs of FIG. 9, a horizontal axis refers to time, and a vertical axis refers to displacement.

According to the present embodiment, a first setting value and a second setting value are determined by a frequency and amplitude of the actuator 810.

When displacement is not appropriate, the processor 120 may re-induce displacement by adjusting at least one of a frequency and amplitude of an actuator, or a combination thereof. For example, in a case where the actuator induces displacement in an object by operating with a frequency and time of the graph of S902, and the induced displacement is small and thus is determined not to be appropriate, the processor 120 may increase compression applied to the object 310 by increasing the amplitude of the actuator 810 (S904) or may increase compression applied to the object 310 by increasing the frequency of the actuator 810 (S906). As another example, the processor 120 may increase compression applied to the object 310 by increasing all of the frequency and the amplitude of the actuator 810 (S908). Which one of the frequency and the amplitude of the actuator 810 is first increased may vary according to embodiments.

Figure 10:
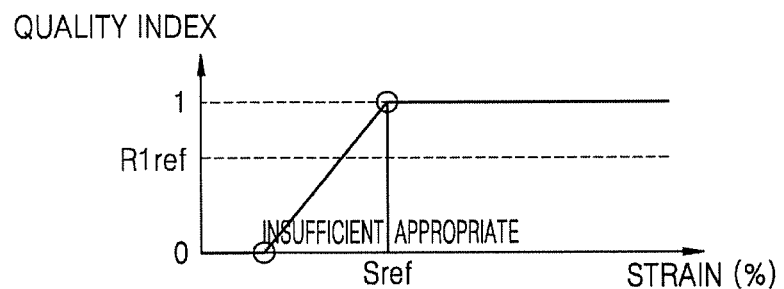
FIG. 10 is a diagram illustrating a determination reference for determining whether an induced displacement is appropriate, according to an embodiment.

FIG. 10 is a diagram illustrating a determination reference for determining whether an induced displacement is appropriate, according to an embodiment.

According to an embodiment, whether induced displacement is appropriate may be determined by using strain. When the strain is equal to or greater than a reference value $S_{ref}$, the processor 120 may determine that the induced displacement is appropriate, and when the strain is less than the reference value $S_{ref}$, the processor 120 may determine that the induced displacement is insufficient and thus is not appropriate.

According to an embodiment, a value of a quality index is determined by the strain, and when the quality index has a value equal to or greater than a reference value $RI_{ref}$, the processor 120 may determine that displacement has been appropriately induced, and when the quality index has a value less than the reference value $RI_{ref}$, the processor 120 may determine that induced displacement is not appropriate.

According to an embodiment, the strain may use an average value in a space. For example, the strain may be an average value of a preset area in an elastic image. According to another embodiment, the strain may be an average in one period of a strain average obtained in one frame or may be a maximum value in one period.

Figure 11:
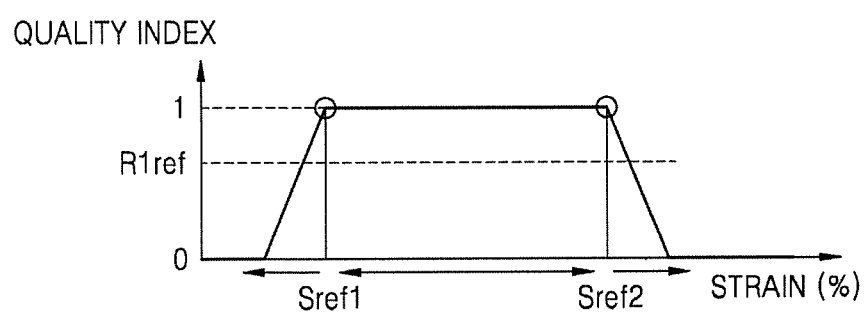
FIG. 11 is a diagram illustrating a determination reference for determining whether an induced displacement is appropriate, according to an embodiment.

FIG. 11 is a diagram illustrating a determination reference for determining whether an induced displacement is appropriate, according to an embodiment. In a graph of FIG. 11, a horizontal axis of the graph indicates strain, and a vertical axis indicates a quality index.

According to an embodiment, when the strain is equal to or greater than a first reference value $S_{ref1}$ and is equal to or less than a second reference value $S_{ref2}$, the processor 120 may determine that induced displacement is appropriate, and when the strain is less than the first reference value $S_{ref1}$ or is greater than the second reference value $S_{ref2}$, the processor 120 may determine that the induced displacement is not appropriate.

According to an embodiment, a value of the quality index is determined by the strain, and when the quality index has a value equal to or greater than a reference value $RI_{ref}$, the processor 120 may determine that displacement has been appropriately induced, and when the quality index has a value less than the reference value $RI_{ref}$, the processor 120 may determine that induced displacement is not appropriate.

Figure 12:
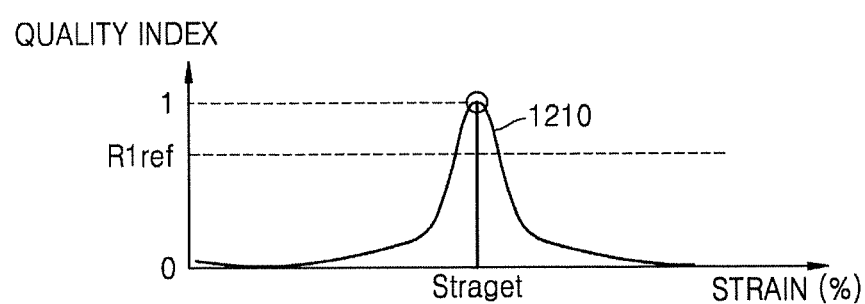
FIG. 12 is a diagram illustrating a determination reference for determining whether an induced displacement is appropriate, according to an embodiment.

FIG. 12 is a diagram illustrating a determination reference for determining whether an induced displacement is appropriate, according to an embodiment. In a graph of FIG. 12, a horizontal axis of the graph indicates strain, and a vertical axis indicates a quality index.

According to an embodiment, a graph of the quality index with respect to the strain may have a Gaussian curve 1210 having a peak at a target reference value $S_{target}$. The processor 120 may calculate the strain from an ultrasound image, applies the calculated strain to the Gaussian curve 1210, and thus calculates the quality index. When the quality index has a value equal to or greater than a reference value $RI_{ref}$, the processor 120 may determine that displacement has been appropriately induced, and when the quality index has a value less than the reference value $RI_{ref}$, the processor 120 may determine that induced displacement is not appropriate.

When a strain average is too small, an SNR of a strain image may be insufficient, and when the strain average is too large, a strain may be distorted. According to the present embodiment, strain may be maintained in an appropriate range.

Figure 13:
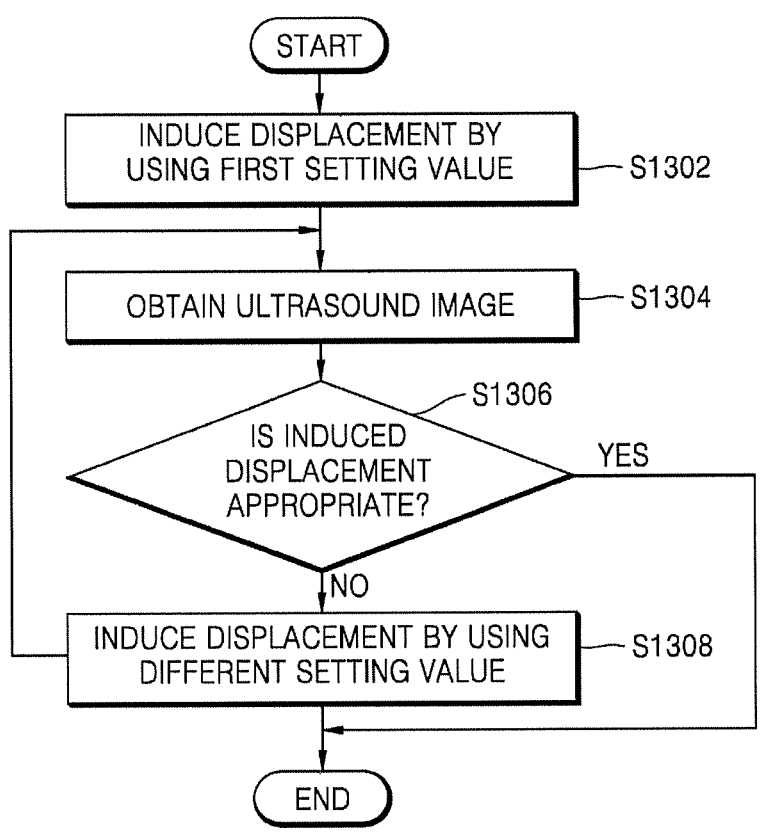
FIG. 13 is a flowchart illustrating an ultrasound diagnostic apparatus control method according to an embodiment.

FIG. 13 is a flowchart illustrating an ultrasound diagnostic apparatus control method according to an embodiment.

Operations of the ultrasound diagnostic apparatus control method may be performed by an ultrasound diagnostic apparatus including a processor enabled to perform image processing, and a storage medium. In the present specification, an embodiment in which the ultrasound diagnostic apparatus 100a or 100b according to the embodiments performs the ultrasound diagnostic apparatus control method will now be described.

Thus, the embodiments described with reference to the ultrasound diagnostic apparatus 100a or 100b may be applied to the ultrasound diagnostic apparatus control method, and on the other hand, embodiments described with reference to the ultrasound diagnostic apparatus control method may be applied to the embodiments described with reference to the ultrasound diagnostic apparatus 100a or 100b. The ultrasound diagnostic apparatus control method according to the embodiments is performed by the ultrasound diagnostic apparatus 100a or 100b disclosed in the present specification but is not limited thereto, thus, the ultrasound diagnostic apparatus control method may be performed by various ultrasound diagnostic apparatuses. Descriptions that have been provided with reference to the ultrasound diagnostic apparatus 100a or 100b are not provided here.

The ultrasound diagnostic apparatus 100 induces displacement in an object by using a first setting value (S1302). According to some embodiments, the ultrasound diagnostic apparatus 100 may induce displacement in the object by using an ultrasound focused beam, or may induce displacement in the object by using an actuator.

Next, the ultrasound diagnostic apparatus 100 obtains an ultrasound image after the displacement in the object is induced (S1304). The ultrasound diagnostic apparatus 100 may obtain the ultrasound image from an eco signal obtained by the probe 20.

The ultrasound diagnostic apparatus 100 determines, from the obtained ultrasound image, whether the induced displacement is appropriate (S1306). The ultrasound diagnostic apparatus 100 determines whether the induced displacement is appropriate, by using a value such as a magnitude of the displacement, strain, a quality index, or the like.

When the induced displacement is not appropriate, the ultrasound diagnostic apparatus 100 induces displacement in the object by using a second setting value different form the first setting value (S1308). When the displacement in the object is induced by using the second setting value, the ultrasound diagnostic apparatus 100 repeats an operation of obtaining an ultrasound image (S1304). According to some embodiments, until induced displacement is determined to be appropriate, the operation of obtaining an ultrasound image may be repeated while a setting value for inducing displacement is changed.

According to the present embodiment, strain may be maintained in an appropriate range.

The ultrasound diagnostic apparatus and the control method therefor of the present disclosure may be embodied as computer-readable codes on a computer-readable recording medium. The computer-readable recording medium is any data storage device that can store data which can be thereafter read by a computer system. Examples of the computer-readable recording medium include read-only memory (ROM), random-access memory (RAM), CD-ROMs, magnetic tapes, floppy disks, optical data storage devices, etc. and may also include implementation as carrier waves such as data transmission through the Internet. The computer-readable recording medium may be distributed over network-connected computer systems so that the computer-readable codes are stored and executed in a distributed fashion.

While the present disclosure has been particularly shown and described with reference to embodiments thereof, it will be understood by those of ordinary skill in the art that various changes in form and details may be made therein without departing from the spirit and scope of the present disclosure as defined by the following claims.

The invention claimed is:

1. An ultrasound diagnostic apparatus comprising:
a probe configured to induce a first displacement in tissue of an object by irradiating a first focused beam of a first setting value to the object; and
a processor configured to:
obtain a first ultrasound image of the object in which the first displacement has been induced;
determine whether the first displacement is in a range of a predetermined reference based on the obtained first ultrasound image;
control the probe to irradiate a second focused beam of a second setting value different from the first setting value to the object when the first displacement is not in the range of the predetermined reference, so as to induce a second displacement in the tissue of the object; and
process a second ultrasound image of the object in which the second displacement has been induced by the second focused beam,
wherein the processor determines that the first displacement is in the range of the predetermined reference when at least one of a quality index of the first ultrasound image or a strain of the object is greater than or equal to a predetermined reference value, and
wherein the quality index is determined according to a speed of a shear wave induced by irradiating the first focused beam to the object.

2. The ultrasound diagnostic apparatus of claim 1, wherein, when the first displacement induced by the first focused beam is not in the range of the predetermined reference, the processor is further configured to adjust at least one of a voltage or a number of cycles of the second focused beam.

3. The ultrasound diagnostic apparatus of claim 1, wherein, when an obstacle interfering movement of a shear wave induced by the second displacement is detected in the second ultrasound image, the processor is further configured to control the probe to change a horizontal focusing position of the second focused beam.

4. The ultrasound diagnostic apparatus of claim 1, further comprising a display configured to display information about a focusing position of at least one of the first focused beam or the second focused beam, and information about variation in the focusing position.

5. The ultrasound diagnostic apparatus of claim 1, further comprising an actuator configured to induce a third displacement by applying a mechanical force to the object.

6. The ultrasound diagnostic apparatus of claim 1, further comprising a display configured to display at least one of an intensity for inducing the first displacement, an intensity for inducing the second displacement, a magnitude of the first displacement, a magnitude of the second displacement, or the strain.

7. An ultrasound diagnostic apparatus control method comprising:
- inducing a first displacement in tissue of an object by irradiating a first focused beam of a first setting value to the object;
- obtaining a first ultrasound image of the object in which the first displacement has been induced;
- determining whether the first displacement is in a range of a predetermined reference based on the obtained first ultrasound image;
- irradiating a second focused beam of a second setting value different from the first setting value to the object when the first displacement is not in the range of the predetermined reference, so as to induce a second displacement in the tissue of the object; and
- obtaining a second ultrasound image of the object in which the second displacement has been induced by the second focused beam,
- wherein the determining whether the first displacement is in the range of the predetermined reference comprises determining that the first displacement is in the range of the predetermined reference when at least one of a quality index of the first ultrasound image or a strain of the object is greater than or equal to a predetermined reference value, and
- wherein the quality index is determined according to a speed of a shear wave induced by irradiating the first focused beam to the object.

8. The ultrasound diagnostic apparatus control method of claim 7, further comprising, when the first displacement induced by the first focused beam is not in the range of the predetermined reference, adjusting at least one of a voltage or a number of cycles of the second focused beam.

9. The ultrasound diagnostic apparatus control method of claim 7, further comprising, when an obstacle interfering movement of a shear wave induced by the second displacement is detected in the second ultrasound image, changing a horizontal focusing position of the second focused beam.

10. The ultrasound diagnostic apparatus control method of claim 7, further comprising displaying information about a focusing position of at least one of the first focused beam or the second focused beam, and information about variation in the focusing position.

11. A non-transitory computer-readable recording medium storing computer program codes for performing an ultrasound diagnostic apparatus control method comprising:
- inducing a first displacement in tissue of an object by irradiating a first focused beam of a first setting value to the object;
- obtaining a first ultrasound image of the object in which the first displacement has been induced;
- determining whether the first displacement is in a range of a predetermined reference based on the obtained first ultrasound image;
- irradiating a second focused beam of a second setting value different from the first setting value to the object when the first displacement is not in the range of the predetermined reference, so as to induce a second displacement in the tissue of the object; and
- obtaining a second ultrasound image of the object in which the second displacement has been induced by the second focused beam,
- wherein the determining whether the first displacement is in the range of the predetermined reference comprises determining that the first displacement is in the range of the predetermined reference when at least one of a quality index of the first ultrasound image or a strain of the object is greater than or equal to a predetermined reference value, and
- wherein the quality index is determined according to a speed of a shear wave induced by irradiating the first focused beam to the object.

* * * * *